(12) United States Patent
Flyash et al.

(10) Patent No.: US 9,504,826 B2
(45) Date of Patent: Nov. 29, 2016

(54) SKIN TREATMENT APPARATUS FOR PERSONAL USE AND METHOD FOR USING SAME

(75) Inventors: Lion Flyash, Nazareth Illit (IL); Boris Vaynberg, Zikron Yaakov (IL)

(73) Assignee: Syneron Medical LTD, Yoqneam Illit (IL)

( * ) Notice: Subject to any disclaimer, the term of this patent is extended or adjusted under 35 U.S.C. 154(b) by 1077 days.

(21) Appl. No.: 13/177,509

(22) Filed: Jul. 6, 2011

(65) Prior Publication Data

US 2011/0264173 A1  Oct. 27, 2011

Related U.S. Application Data

(62) Division of application No. 12/388,309, filed on Feb. 18, 2009, now Pat. No. 8,606,366.

(51) Int. Cl.

| A61N 1/36 | (2006.01) |
|---|---|
| A61N 1/32 | (2006.01) |
| A61B 18/20 | (2006.01) |
| A61N 1/40 | (2006.01) |
| A61B 18/00 | (2006.01) |
| A61N 1/375 | (2006.01) |
| A61N 5/06 | (2006.01) |

(52) U.S. Cl.
CPC ............. *A61N 1/328* (2013.01); *A61B 18/203* (2013.01); *A61N 1/40* (2013.01); *A61B 2018/0047* (2013.01); *A61B 2018/00452* (2013.01); *A61N 1/36014* (2013.01); *A61N 1/3756* (2013.01); *A61N 2005/0659* (2013.01)

(58) Field of Classification Search
CPC ............. A61B 2018/00452; A61B 2018/0047; A61N 1/328; A61N 1/40; A61N 5/0616

USPC ........................................................ 606/11, 9
See application file for complete search history.

(56) References Cited

U.S. PATENT DOCUMENTS

| 1,430,354 A | 9/1922 | Burdick |
|---|---|---|
| 2,183,726 A | 2/1939 | Sommer et al. |
| 2,231,095 A | 2/1941 | Sommer et al. |
| 2,824,308 A | 2/1958 | Duncan |
| 3,088,205 A | 5/1963 | Ellis |

(Continued)

FOREIGN PATENT DOCUMENTS

| CA | 2495005 A1 | 2/2004 |
|---|---|---|
| CN | 1078383 A | 11/1993 |

(Continued)

OTHER PUBLICATIONS

Acne Clearance, LHE Clinical Casebook, Radiancy: Lighting the Future of Skin Care, © 2002.

(Continued)

*Primary Examiner* — Laura Bouchelle
*Assistant Examiner* — Anh Bui
(74) *Attorney, Agent, or Firm* — Smith Tempel Blaha LLC; Gregory Scott Smith

(57) ABSTRACT

An apparatus for personal skin treatment includes an RF generator and an applicator with at least a pair of electrodes mounted on the distal end of the applicator. The electrodes are configured for applying an RF voltage to a subject skin. The RF voltage generator supplies the electrodes with the RF voltage. The applicator includes a source of illumination illuminating the treated skin segment.

13 Claims, 15 Drawing Sheets

(56) References Cited

U.S. PATENT DOCUMENTS

| | | |
|---|---|---|
| D196,532 S | 10/1963 | Facci |
| 3,925,739 A * | 12/1975 | Brownell ............... H03H 7/09 |
| | | 333/176 |
| 3,946,738 A * | 3/1976 | Newton et al. ............... 606/34 |
| 3,964,482 A | 6/1976 | Gerstel et al. |
| 4,016,886 A | 4/1977 | Doss et al. |
| 4,182,329 A | 1/1980 | Smit et al. |
| D269,294 S | 6/1983 | Rakocy et al. |
| D271,015 S | 10/1983 | Geraets |
| D271,199 S | 11/1983 | Geraets |
| 4,444,190 A | 4/1984 | Mutzhas |
| D274,462 S | 6/1984 | Rakocy et al. |
| 4,553,936 A | 11/1985 | Wang |
| 4,686,986 A | 8/1987 | Fenyo et al. |
| 4,753,958 A | 6/1988 | Weinstein et al. |
| 4,755,361 A | 7/1988 | Fuderer |
| 4,784,135 A | 11/1988 | Blum et al. |
| 4,837,027 A | 6/1989 | Lee et al. |
| 4,858,604 A * | 8/1989 | Konishi ............... 602/57 |
| 4,867,682 A | 9/1989 | Hammesfahr et al. |
| 4,869,584 A | 9/1989 | Dion |
| 4,943,290 A | 7/1990 | Rexroth et al. |
| 5,016,999 A | 5/1991 | Williams |
| 5,019,034 A | 5/1991 | Weaver et al. |
| 5,165,418 A | 11/1992 | Tankovich |
| 5,169,384 A | 12/1992 | Bosrnak et al. |
| 5,196,709 A | 3/1993 | Berndt et al. |
| 5,232,441 A | 8/1993 | Stephen et al. |
| 5,246,867 A | 9/1993 | Lakowicz et al. |
| 5,281,825 A | 1/1994 | Berndt et al. |
| 5,286,479 A | 2/1994 | Garlich et al. |
| 5,316,473 A | 5/1994 | Hare |
| 5,318,514 A | 6/1994 | Hofmann |
| 5,328,478 A | 7/1994 | Mc Vay |
| 5,380,272 A | 1/1995 | Gross |
| 5,401,242 A * | 3/1995 | Yacowitz ............... 604/48 |
| 5,402,697 A | 4/1995 | Brooks |
| 5,406,340 A | 4/1995 | Hoff |
| 5,409,835 A | 4/1995 | Lakowicz et al. |
| 5,418,130 A | 5/1995 | Platz et al. |
| 5,421,817 A | 6/1995 | Liss et al. |
| 5,423,803 A | 6/1995 | Tankovich et al. |
| 5,439,440 A | 8/1995 | Hofmann |
| 5,445,609 A | 8/1995 | Lattin et al. |
| 5,445,611 A | 8/1995 | Eppstein et al. |
| 5,458,140 A | 10/1995 | Eppstein et al. |
| 5,462,520 A | 10/1995 | Hofmann |
| 5,464,386 A | 11/1995 | Hofmann |
| 5,485,530 A | 1/1996 | Lakowicz et al. |
| 5,487,662 A | 1/1996 | Kipke et al. |
| 5,500,437 A | 3/1996 | Saitoh et al. |
| 5,521,392 A | 5/1996 | Kennedy et al. |
| 5,552,300 A | 9/1996 | Makrides et al. |
| 5,571,149 A | 11/1996 | Liss et al. |
| 5,582,168 A | 12/1996 | Samuels et al. |
| 5,582,476 A | 12/1996 | Hansen |
| 5,611,793 A | 3/1997 | Wilson et al. |
| 5,624,847 A | 4/1997 | Lakowicz et al. |
| 5,628,310 A | 5/1997 | Rao et al. |
| 5,628,771 A | 5/1997 | Mizukawa et al. |
| 5,631,169 A | 5/1997 | Lakowicz et al. |
| 5,642,997 A | 7/1997 | Gregg et al. |
| 5,648,269 A | 7/1997 | Lakowicz et al. |
| 5,658,148 A | 8/1997 | Neuberger et al. |
| 5,660,997 A | 8/1997 | Spaulding |
| 5,666,543 A | 9/1997 | Gartland |
| 5,674,267 A | 10/1997 | Mir et al. |
| 5,681,282 A | 10/1997 | Eggers et al. |
| 5,688,232 A | 11/1997 | Flower |
| 5,697,896 A | 12/1997 | McNichols et al. |
| 5,698,217 A | 12/1997 | Wilking |
| 5,698,866 A | 12/1997 | Doiron et al. |
| 5,704,935 A | 1/1998 | Pahl et al. |
| 5,707,403 A | 1/1998 | Grove et al. |
| 5,720,772 A | 2/1998 | Eckhouse |
| 5,722,397 A | 3/1998 | Eppstein |
| 5,722,411 A | 3/1998 | Suzuki et al. |
| 5,735,844 A | 4/1998 | Anderson et al. |
| 5,755,753 A | 5/1998 | Knowlton |
| 5,759,767 A | 6/1998 | Lakowicz et al. |
| 5,769,880 A | 6/1998 | Truckai et al. |
| 5,792,049 A | 8/1998 | Eppstein et al. |
| 5,814,008 A | 9/1998 | Chen et al. |
| 5,824,023 A | 10/1998 | Anderson |
| 5,836,999 A | 11/1998 | Eckhouse et al. |
| 5,843,143 A | 12/1998 | Whitehurst |
| 5,860,421 A | 1/1999 | Eppstein et al. |
| 5,871,469 A | 2/1999 | Eggers et al. |
| 5,871,524 A | 2/1999 | Knowlton |
| 5,873,855 A | 2/1999 | Eggers et al. |
| 5,885,211 A | 3/1999 | Eppstein et al. |
| 5,902,272 A | 5/1999 | Eggers et al. |
| 5,911,223 A | 6/1999 | Weaver et al. |
| 5,919,219 A | 7/1999 | Knowlton |
| 5,924,981 A | 7/1999 | Rothfritz et al. |
| 5,938,657 A | 8/1999 | Assa et al. |
| 5,949,514 A | 9/1999 | Wargon |
| 5,954,710 A | 9/1999 | Paolini et al. |
| 5,961,543 A | 10/1999 | Waldmann |
| 5,964,726 A | 10/1999 | Korenstein et al. |
| 5,980,898 A | 11/1999 | Plenn et al. |
| 5,983,130 A | 11/1999 | Phipps et al. |
| 5,983,131 A | 11/1999 | Weaver et al. |
| 5,983,135 A | 11/1999 | Avrahami |
| 5,984,915 A | 11/1999 | Loeb et al. |
| 5,993,180 A | 11/1999 | Westerhof et al. |
| 6,002,482 A | 12/1999 | Rothfritz et al. |
| 6,009,344 A | 12/1999 | Flower et al. |
| 6,022,316 A | 2/2000 | Eppstein et al. |
| 6,024,733 A | 2/2000 | Eggers et al. |
| 6,030,399 A | 2/2000 | Ignotz et al. |
| 6,041,253 A | 3/2000 | Kost et al. |
| 6,045,502 A | 4/2000 | Eppstein et al. |
| 6,050,988 A | 4/2000 | Zuck |
| 6,055,451 A | 4/2000 | Bambot et al. |
| 6,056,548 A | 5/2000 | Neuberger et al. |
| 6,063,108 A | 5/2000 | Salansky et al. |
| 6,066,134 A | 5/2000 | Eggers et al. |
| 6,076,012 A | 6/2000 | Swanson et al. |
| 6,080,127 A | 6/2000 | Li et al. |
| 6,080,391 A | 6/2000 | Tsuchiya et al. |
| 6,081,934 A | 7/2000 | Stefanovsky et al. |
| 6,083,196 A | 7/2000 | Trautman et al. |
| 6,088,606 A | 7/2000 | Ignotz et al. |
| 6,090,106 A | 7/2000 | Goble et al. |
| 6,104,952 A | 8/2000 | Tu et al. |
| 6,107,326 A | 8/2000 | Jori |
| 6,117,109 A | 9/2000 | Eggers et al. |
| 6,132,701 A | 10/2000 | Perez et al. |
| 6,142,922 A | 11/2000 | Yoshikawa et al. |
| 6,142,939 A | 11/2000 | Eppstein et al. |
| 6,148,232 A | 11/2000 | Avrahami |
| 6,159,194 A | 12/2000 | Eggers et al. |
| 6,169,224 B1 | 1/2001 | Heinecke et al. |
| 6,173,202 B1 | 1/2001 | Eppstein |
| 6,183,434 B1 | 2/2001 | Eppstein |
| 6,190,609 B1 | 2/2001 | Chapman et al. |
| 6,191,110 B1 | 2/2001 | Jaynes et al. |
| 6,192,734 B1 | 2/2001 | Rothfritz et al. |
| 6,210,402 B1 | 4/2001 | Olsen et al. |
| 6,221,095 B1 | 4/2001 | Van Zuylen et al. |
| 6,228,078 B1 | 5/2001 | Eggers et al. |
| 6,231,593 B1 | 5/2001 | Meserol |
| 6,235,020 B1 | 5/2001 | Cheng et al. |
| 6,238,391 B1 | 5/2001 | Olsen et al. |
| 6,251,127 B1 | 6/2001 | Biel |
| 6,258,319 B1 | 7/2001 | Hearst et al. |
| 6,288,498 B1 | 9/2001 | Cheng |
| 6,302,874 B1 | 10/2001 | Zhang et al. |
| 6,308,413 B1 | 10/2001 | Westerhof et al. |
| 6,339,775 B1 | 1/2002 | Zamanian et al. |
| 6,343,400 B1 | 2/2002 | Massholder et al. |
| 6,343,933 B1 | 2/2002 | Montgomery et al. |
| 6,352,506 B1 | 3/2002 | Eppstein et al. |

(56) References Cited

U.S. PATENT DOCUMENTS

| | | |
|---|---|---|
| 6,353,763 B1 | 3/2002 | George et al. |
| 6,406,157 B1 | 6/2002 | Audet |
| 6,413,268 B1 | 7/2002 | Hartman |
| 6,425,912 B1 | 7/2002 | Knowlton |
| 6,433,343 B1 | 8/2002 | Cimino et al. |
| 6,440,121 B1 | 8/2002 | Weber et al. |
| 6,461,567 B1 | 10/2002 | Hearst et al. |
| 6,462,070 B1 | 10/2002 | Hasan et al. |
| 6,471,716 B1 | 10/2002 | Pecukonis |
| 6,477,410 B1 | 11/2002 | Henley et al. |
| 6,487,447 B1 | 11/2002 | Weimann et al. |
| 6,493,940 B2 | 12/2002 | Westerhof et al. |
| 6,494,900 B1 | 12/2002 | Salansky et al. |
| 6,497,702 B1 | 12/2002 | Bernaz |
| 6,508,785 B1 | 1/2003 | Eppstein |
| 6,508,813 B1 | 1/2003 | Altshuler |
| 6,512,950 B2 | 1/2003 | Li et al. |
| 6,514,243 B1 | 2/2003 | Eckhouse et al. |
| 6,517,532 B1 | 2/2003 | Altshuler et al. |
| 6,527,716 B1 | 3/2003 | Eppstein |
| 6,530,915 B1 | 3/2003 | Eppstein et al. |
| 6,533,775 B1 | 3/2003 | Rizoiu et al. |
| 6,558,653 B2 | 5/2003 | Andersen et al. |
| 6,572,637 B1 | 6/2003 | Yamazaki et al. |
| 6,594,905 B2 | 7/2003 | Furst et al. |
| 6,595,947 B1 | 7/2003 | Mikszta et al. |
| 6,597,946 B2 | 7/2003 | Avrahami et al. |
| 6,602,245 B1 | 8/2003 | Thiberg |
| 6,603,998 B1 | 8/2003 | King et al. |
| 6,611,706 B2 | 8/2003 | Avrahami et al. |
| 6,611,707 B1 | 8/2003 | Prausnitz et al. |
| 6,612,819 B1 | 9/2003 | Furst et al. |
| 6,615,079 B1 | 9/2003 | Avrahami |
| 6,618,620 B1 | 9/2003 | Freundlich et al. |
| 6,632,002 B1 | 10/2003 | Chubb et al. |
| 6,637,877 B1 | 10/2003 | Hartley et al. |
| 6,662,054 B2 | 12/2003 | Kreindel et al. |
| 6,663,620 B2 | 12/2003 | Altshuler et al. |
| 6,676,655 B2 | 1/2004 | McDaniel |
| 6,678,554 B1 | 1/2004 | Sun et al. |
| 6,692,456 B1 | 2/2004 | Eppstein et al. |
| 6,702,808 B1 | 3/2004 | Kreindel |
| 6,704,587 B1 | 3/2004 | Kumar et al. |
| 6,706,693 B1 | 3/2004 | Tang et al. |
| 6,708,060 B1 | 3/2004 | Avrahami et al. |
| 6,711,435 B2 | 3/2004 | Avrahami |
| 6,713,291 B2 | 3/2004 | King et al. |
| 6,719,754 B2 | 4/2004 | Underwood et al. |
| D490,156 S | 5/2004 | Fischer et al. |
| D490,526 S | 5/2004 | Jonsen |
| 6,743,211 B1 * | 6/2004 | Prausnitz et al. ............ 604/239 |
| 6,758,845 B1 | 7/2004 | Weckwerth et al. |
| 6,761,729 B2 | 7/2004 | Babaev |
| 6,767,341 B2 | 7/2004 | Cho |
| 6,770,069 B1 | 8/2004 | Hobart et al. |
| 6,773,431 B2 | 8/2004 | Eggers et al. |
| 6,780,838 B2 | 8/2004 | Lipton et al. |
| 6,795,728 B2 | 9/2004 | Chornenky et al. |
| RE38,634 E | 10/2004 | Westerhof et al. |
| 6,887,260 B1 | 5/2005 | McDaniel |
| 6,889,090 B2 | 5/2005 | Kreindel |
| 7,006,874 B2 | 2/2006 | Knowlton et al. |
| 7,013,179 B2 | 3/2006 | Carter et al. |
| 7,062,317 B2 | 6/2006 | Avrahami et al. |
| 7,123,957 B2 | 10/2006 | Avrahami |
| 7,153,298 B1 | 12/2006 | Cohen |
| 7,164,942 B2 | 1/2007 | Avrahami et al. |
| 7,234,239 B2 | 6/2007 | Saito et al. |
| 7,266,414 B2 | 9/2007 | Cornelius et al. |
| 7,275,819 B2 | 10/2007 | Bleau |
| 7,314,470 B2 * | 1/2008 | Malodobry .................. 606/131 |
| 7,335,377 B2 | 2/2008 | Stern et al. |
| 7,363,075 B2 | 4/2008 | Stern et al. |
| 7,383,084 B2 | 6/2008 | Stern et al. |
| 7,395,111 B2 | 7/2008 | Levin et al. |
| 7,415,306 B2 | 8/2008 | Levin et al. |
| 7,435,247 B2 | 10/2008 | Woloszko et al. |
| 7,494,488 B2 | 2/2009 | Weber |
| 7,558,625 B2 | 7/2009 | Levin et al. |
| 7,963,985 B2 | 6/2011 | Minamoto et al. |
| 8,135,475 B2 | 3/2012 | Kreindel et al. |
| 8,157,807 B2 | 4/2012 | Ferren et al. |
| 8,202,268 B1 | 6/2012 | Wells et al. |
| 2001/0006645 A1 | 7/2001 | Norton et al. |
| 2001/0051180 A1 | 12/2001 | Watanabe et al. |
| 2002/0010412 A1 | 1/2002 | Eppstein |
| 2002/0010414 A1 | 1/2002 | Coston et al. |
| 2002/0082543 A1 | 6/2002 | Park et al. |
| 2002/0091311 A1 | 7/2002 | Eppstein et al. |
| 2002/0099308 A1 | 7/2002 | Bojan et al. |
| 2002/0104543 A1 | 8/2002 | Hollander et al. |
| 2002/0120256 A1 | 8/2002 | Furuno et al. |
| 2002/0143373 A1 | 10/2002 | Courtnage et al. |
| 2002/0161324 A1 | 10/2002 | Henley et al. |
| 2002/0169394 A1 | 11/2002 | Eppstein et al. |
| 2002/0183245 A1 | 12/2002 | Hasan et al. |
| 2002/0190337 A1 | 12/2002 | House et al. |
| 2002/0193729 A1 | 12/2002 | Cormier et al. |
| 2002/0198575 A1 | 12/2002 | Sullivan |
| 2003/0017598 A1 | 1/2003 | Burke et al. |
| 2003/0032950 A1 | 2/2003 | Altshuler et al. |
| 2003/0078499 A1 | 4/2003 | Eppstein |
| 2003/0092982 A1 | 5/2003 | Eppstein |
| 2003/0097162 A1 | 5/2003 | Kreindel |
| 2003/0109871 A1 | 6/2003 | Johnson et al. |
| 2003/0135250 A1 | 7/2003 | Lauman et al. |
| 2003/0139790 A1 | 7/2003 | Ingle et al. |
| 2003/0195494 A1 | 10/2003 | Altshuler et al. |
| 2003/0199946 A1 | 10/2003 | Gutwein |
| 2004/0010250 A1 | 1/2004 | Manna et al. |
| 2004/0010298 A1 | 1/2004 | Altshuler et al. |
| 2004/0028727 A1 | 2/2004 | Glenn et al. |
| 2004/0039342 A1 | 2/2004 | Eppstein et al. |
| 2004/0039343 A1 | 2/2004 | Eppstein et al. |
| 2004/0064167 A1 | 4/2004 | Berry et al. |
| 2004/0133251 A1 | 7/2004 | Altshuler et al. |
| 2004/0143308 A1 | 7/2004 | Lundahl et al. |
| 2004/0147984 A1 | 7/2004 | Altshuler et al. |
| 2004/0167501 A1 | 8/2004 | Island et al. |
| 2004/0185055 A1 | 9/2004 | Glenn et al. |
| 2004/0193234 A1 | 9/2004 | Butler |
| 2004/0210214 A1 | 10/2004 | Knowlton |
| 2004/0258703 A1 | 12/2004 | Glenn et al. |
| 2004/0260210 A1 | 12/2004 | Ella et al. |
| 2005/0015042 A1 | 1/2005 | Sun et al. |
| 2005/0043653 A1 | 2/2005 | Trimmer et al. |
| 2005/0049543 A1 | 3/2005 | Anderson et al. |
| 2005/0119605 A1 | 6/2005 | Sohn |
| 2005/0123565 A1 | 6/2005 | Subramony et al. |
| 2005/0137654 A1 | 6/2005 | Hoenig et al. |
| 2005/0137655 A1 | 6/2005 | MacFarland et al. |
| 2005/0143793 A1 | 6/2005 | Korman et al. |
| 2005/0147137 A1 | 7/2005 | Slatkine |
| 2005/0177139 A1 | 8/2005 | Yamazaki et al. |
| 2006/0036300 A1 | 2/2006 | Kreindel |
| 2006/0095096 A1 | 5/2006 | DeBenedictis et al. |
| 2006/0149343 A1 | 7/2006 | Altshuler et al. |
| 2006/0173518 A1 * | 8/2006 | Kreindel ................ A61B 18/14 607/101 |
| 2006/0200213 A1 | 9/2006 | McDaniel |
| 2006/0206173 A1 | 9/2006 | Gertner et al. |
| 2006/0224217 A1 | 10/2006 | Burgmann et al. |
| 2006/0231568 A1 | 10/2006 | Lynn et al. |
| 2006/0247741 A1 | 11/2006 | Hsu et al. |
| 2006/0259102 A1 * | 11/2006 | Slatkine ..................... 607/88 |
| 2007/0009542 A1 | 1/2007 | Levin et al. |
| 2007/0016117 A1 | 1/2007 | Sliwa et al. |
| 2007/0031495 A1 | 2/2007 | Eppstein et al. |
| 2007/0093798 A1 | 4/2007 | Debenedictis et al. |
| 2007/0106349 A1 | 5/2007 | Karni et al. |
| 2007/0129711 A1 | 6/2007 | Altshuler et al. |
| 2007/0142881 A1 | 6/2007 | Hennings |
| 2007/0191821 A1 | 8/2007 | Boxer Wachler |

(56) References Cited

U.S. PATENT DOCUMENTS

| | | | |
|---|---|---|---|
| 2007/0191827 A1* | 8/2007 | Lischinsky | A61B 18/1206 606/34 |
| 2007/0197895 A1 | 8/2007 | Nycz et al. | |
| 2007/0239143 A1 | 10/2007 | Altshuler et al. | |
| 2007/0270732 A1 | 11/2007 | Levin et al. | |
| 2007/0271714 A1 | 11/2007 | Adam et al. | |
| 2007/0287949 A1 | 12/2007 | Levin et al. | |
| 2007/0292445 A1 | 12/2007 | Levin | |
| 2008/0071334 A1 | 3/2008 | Hoenig et al. | |
| 2008/0114281 A1 | 5/2008 | Birchall et al. | |
| 2008/0123238 A1 | 5/2008 | Campos et al. | |
| 2008/0208107 A1 | 8/2008 | McRae et al. | |
| 2008/0214988 A1 | 9/2008 | Altshuler et al. | |
| 2008/0215124 A1 | 9/2008 | Wagenaar et al. | |
| 2008/0221504 A1 | 9/2008 | Aghion | |
| 2008/0274166 A1 | 11/2008 | Sacks et al. | |
| 2008/0294153 A1 | 11/2008 | Allshuler et al. | |
| 2008/0306476 A1 | 12/2008 | Hennings et al. | |
| 2009/0036953 A1 | 2/2009 | Gustavsson | |
| 2009/0043293 A1 | 2/2009 | Pankratov et al. | |
| 2009/0105706 A1 | 4/2009 | Livneh | |
| 2009/0112205 A1 | 4/2009 | McGill et al. | |
| 2009/0182315 A1 | 7/2009 | Zigan et al. | |
| 2009/0192503 A1 | 7/2009 | Epshtein et al. | |
| 2009/0240310 A1 | 9/2009 | Kennedy | |
| 2009/0264810 A1 | 10/2009 | Eppstein et al. | |
| 2010/0063565 A1 | 3/2010 | Beerwerth et al. | |
| 2010/0174224 A1 | 7/2010 | Sohn | |
| 2010/0198134 A1* | 8/2010 | Eckhouse | B26B 19/46 604/20 |
| 2010/0274329 A1 | 10/2010 | Bradley et al. | |
| 2010/0293807 A1 | 11/2010 | Bar-El et al. | |
| 2011/0137386 A1 | 6/2011 | Kreindel | |
| 2011/0166559 A1 | 7/2011 | Eckhouse et al. | |
| 2012/0143270 A1 | 6/2012 | Mehta | |
| 2012/0290023 A1 | 11/2012 | Boyden et al. | |
| 2013/0289679 A1 | 10/2013 | Eckhouse et al. | |

FOREIGN PATENT DOCUMENTS

| | | |
|---|---|---|
| EP | 547482 A1 | 6/1993 |
| EP | 0743029 B1 | 7/2002 |
| EP | 0824019 B1 | 11/2002 |
| GB | 2125986 A | 8/1982 |
| GB | 2202442 A | 9/1988 |
| JP | 04299998 A2 | 10/1992 |
| JP | 06007457 | 1/1994 |
| JP | 06113920 A2 | 4/1994 |
| JP | 11132843 A2 | 12/1999 |
| JP | 2003034630 | 2/2003 |
| WO | WO-9310854 A1 | 6/1993 |
| WO | WO-93/21992 A1 | 11/1993 |
| WO | WO-9414062 A1 | 6/1994 |
| WO | WO-9416765 A1 | 8/1994 |
| WO | WO-9427671 A1 | 12/1994 |
| WO | WO-96/22808 A1 | 1/1996 |
| WO | WO-9617651 A1 | 6/1996 |
| WO | WO-9640364 A1 | 12/1996 |
| WO | WO-9707734 A1 | 3/1997 |
| WO | WO-9716222 A1 | 5/1997 |
| WO | WO-9800193 A1 | 1/1998 |
| WO | WO-9829134 A2 | 7/1998 |
| WO | WO-99/09143 A1 | 2/1999 |
| WO | WO-9944507 A1 | 9/1999 |
| WO | WO-9944508 A1 | 9/1999 |
| WO | WO-9944637 A1 | 9/1999 |
| WO | WO-9944638 A1 | 9/1999 |
| WO | WO-9944678 A1 | 9/1999 |
| WO | WO-0003758 A1 | 1/2000 |
| WO | WO-0004832 A1 | 2/2000 |
| WO | WO-0015102 A1 | 3/2000 |
| WO | WO-0044438 A1 | 8/2000 |
| WO | WO-0059371 A1 | 10/2000 |
| WO | WO-0074583 A1 | 12/2000 |
| WO | WO-0074763 A2 | 12/2000 |
| WO | WO-0074767 A2 | 12/2000 |
| WO | WO-0076575 A2 | 12/2000 |
| WO | WO-0113989 A1 | 3/2001 |
| WO | WO-0135820 A1 | 5/2001 |
| WO | WO-02/074244 | 9/2002 |
| WO | WO-02/078644 A2 | 10/2002 |
| WO | WO-02090210 A1 | 11/2002 |
| WO | WO-03/039367 A1 | 5/2003 |
| WO | WO-03039620 A2 | 5/2003 |
| WO | WO-2004/039426 A2 | 5/2004 |
| WO | WO-2004/039427 A2 | 5/2004 |
| WO | WO-2004/039428 A2 | 5/2004 |
| WO | WO-2006/128034 A1 | 11/2006 |
| WO | WO-2008091878 A1 | 7/2008 |
| WO | WO-2009047774 A2 | 4/2009 |
| WO | WO-2006131931 A3 | 1/2013 |
| WO | WO-03077970 A3 | 2/2013 |
| WO | WO-03101507 A3 | 3/2013 |
| WO | WO-03077971 A3 | 12/2013 |

OTHER PUBLICATIONS

Acne Star web page, describing "How to use get rid of Acne Treatment", printed May 5, 2005.
Acne Star web page, describing Clinical Studies, "The Treatment of acne vulgaris with a novel device that uses Gallium-Nitride diode light", printed May 5, 2005.
Aesthetic Buyers Guide: The Leading Cosmetic Practice Resource, Jan./Feb. 2004, vol. 7, No. I.
Bollen, CM. et al., "Full- versus partial-mouth disinfection in the treatment of periodontal infections. A pilot study: long-term microbiological observations". J Clin Periodontol Oct. 1996;23(10):960-70 (Abstract).
Bollen, CM. et al., "The effect of a one-stage full-mouth disinfection on different intra-oral niches. Clinical and microbiological observations", J Clin Periodontol Jan. 1998;25(1):56-66 (Abstract).
CALDER1-IEAD, R. Glen, "The Photobiology of LED Phototherapy".
Charakida et al., "Phototherapy in the Treatment of Acne Vulgaris, What is the Role?", Am. J. Clin. Dermatol 2004: 5(4): 211-216.
Cohen LR., "What causes bad breath?", University of Toronto; webpage (printed before Nov. 2, 2004).
Coventry et al. (2000) "ABC of oral health: Periodontal disease" British Medical Journal, 321, 36-39.
De Soete, M. et al., "One-stage full-mouth disinfection. Long-term microbiological results analyzed by checker board DNA-DNA hybridization", J Periodontol Mar. 2001; 72(3):374-82 (Abstract).
Elman M. et al., "The effective treatment of acne vulgaris by a high-intensity, narrow bank 405-420 nm light source", Cosmetic & Laser Ther 2003; 5: 111-116.
Flow Control Network web page, "Mini Diaphragm Pumps for Precision Dispensing" by Ping Lin, printed Aug. 2, 2005.
Friedberg JS et al., "Antibody-Targeted Photolysis Bacteriocidal Effects of Sn (IV) Chlonn e6-Dextran-Monoclonal Antibody Conjugates", Annals New York Academy of Sciences 618:383-393, 1991.
Greenstein G., Full-mouth therapy versus individual quadrant root planning: a critical commentary, JPeriodontol Jul. 2002;73(7):797-812 (Abstract).
Hamblin, M. et al., "Rapid Control of Wound Infections by Targeted Photodynamic Therapy Monitored by In Vivo Bioluminescence Imagining", Photochemistry and Photobiology, 2002, 75(1 ): 51-57.
Komerik et al. (2003) "In vivo killing of Porphyromonas gingivalis by toluidine blue-mediated photosensitization in an animal model" Antimicrobial Agents and Chemotherapy, 47(3), 932-940.
Krespi, et al. (2005) "Lethal photosensitization of oral pathogens via red-filtered halogen lamp" Oral Diseases, 11(S1 ), 92-95.
Malik, Z. et al., "New Trends in Photobiology (Invited Review) Bactericidal Effects of Photoactivated Porphyrins—An Alternative Approach to Antimicrobial Drugs", Journal of Photochemistry and Photobiology, B: Biology, 5_1_1990}_281-293.
Matevski D. et al., "Lethal photosensitization of periodontal pathogens by a red-filtered Xenon lamp in invitro", JPeriodont. Res. 2003. 38:428-435.

(56) References Cited

OTHER PUBLICATIONS

Matevski D. et al., "Sensitivity of Porphyromonas gingivalis to Light-Activated Toluidine Blue 0", University of Toronto, Faculty of Dentistry; Slide presentation (presented before Nov. 15, 2002).
Meisel etal. (2005) "Photodynamic therapy for periodontal diseases: State of the are" J. Photochem. Photobiol., 79, 159-170.
Mongardini, C. et al., "One stage full- versus partial-mouth disinfection in the treatment of chronic adult or generalized early-onset periodontitis. I. Long-term clinical observations", J Periodontol Jun. 1999;70(6):632-45 lAbstrac!2.__.
Morton C.A. et al., An open study to determine the efficacy of blue light in the treatment of mild to moderate acne: preliminary data (publication status unknown).
Nakano et al. (2002) "Correlation between oral malodor and periodontal bacteria" Microbes Infect., 4(6), 679-683.
Ondine Biopharma web page—printed Oct. 15, 2002.
Papageorgiou et al., "Phototherapy with blue (415 nm) and red (660 nm) light in the treatment of acne vulgaris", British Journal of Dermatology 2000: 142: 973-978.
Pharmaceutical description, Levulan® Kerastick aminolevulinic acid I-IC!) for Topical Solution, 20'X.
Quirynen, M. et al. "Full- vs. partial-mouth disinfection in the treatment of periodontal infections: short-term clinical and microbiological observations", J Dent Res Aug. 1995;74(8):1459-67 (Abstract).
Quirynen, M. et al., "The effect of a 1-stage full-mouth disinfection on oral malodor and microbial colonization of the tongue in periodontitis. A pilot study", J Periodontol Mar. 1998;69(3):374-82 (Abstract).
Quirynen, M. et al., "The intra-oral translocation of periodontopathogens jeopardises the outcome of periodontal therapy", Journal of Clincial Periodontology, Jun. 2001, vol. 28, Issue 6, p. 499 (Abstract).
Quirynen, M. et al., "The role of chlorhexidine in the one-stage full-mouth disinfection treatment of patients with advanced adult periodontitis. Long-term clinical and microbiological observations", J Clin Periodontol 2000 Al!JL2~579-89 J__Abstrac__!).
Quirynen. M. et al., "One stage full- versus partial-mouth disinfection in the treatment of chronic adult or generalized early-onset periodontitis. II. Long-term impact on microbial load", J Periodontol Jun. 1999;70(6):646-56 J__Abstrac!2.__.
Sanz et al. (2001) "Fundamentals of breath malodour" Journal of Contemporary Dental Practice, 2(4), 1-13.
Sarkar et al. (1993) "Lethal photosensitization of bacteria in subgingival plaque from patients with chronic periodontitis" J. Periodont. Res , 28, 204-21 O.
Skin91I.corn web page regarding Peter Thomas Roth Clinical Acne Medication, acne treatrnent-Benzoyl Peroxide 5% pbp5, printed Apr. 19, 2005.
Soukos et al. (1998) "Targeted antimicrobial photochemotherapy", Antimicrobial Agents and Chemotherapy 42( 10 ), 2595-2601.
Spire Awarded Contract for Ear Surgery Laser—Press Release Aug. 23, 2002.
Temperatures.corn web page, "Thermistor Temperature Sensors," printed Aug. 2, 200.
Vandekerckhove, BN. et al.. "Full- versus partial-mouth disinfection in the treatment of periodontal infections. Long-term clinical observations of a pilot study", J Periodontol Dec. 1996;67(12):1251-9 (Abstract).
Wainwright M., Photodynamic antimicrobial chemotherapy (PACT), Journal of Antimicrobial Chemotherapy (1998) 42, 13-28.
Wilson (2005) "Lethal photosensitisation of oral bacteria and its potential application in the photodynamic therapy of oral infection" Photochem. Photobiol. Sci., 3, 412-418.
Wilson et al. (1995) "Bacteria in supragingival plaque samples can be killed by low-power laser light in the presence of a photosensitizer" J. Appl. Bacteriol., 78, 569-574.
Wood, et al. (1999) "An in vitro study of the use of photodynamic therapy for the treatment of natural oral plaque biofilrns formed in vivo" J. Photochem. Photogiol. B: Biol., 50, 1-7.
www.lightbioscience.com web page, Gentle Waves Cosmcceuticals, printed Jul. 29, 200.
www.lightbioscience.com web page, Gentle Waves LED Photomodulation Fact Sheet, printed Jul. 29, 2005.
Sintov et al., J. of Controlled Release, 89: 311-320 (2003).
Henry, S. et al., "Micromachined Needles for the Transfermal Delivery of Drugs", IEEE 11th Annual International Workshop on Micro-Electric-Mechanical Systems, 1998, pp. 494-498.
Chizmadzhev, Yuri A., et al., "Electrical Properties of Skin at Moderate Voltages: Contribution of Appendageal Macropores", Biophysical Journal, Feb. 1998, vol. 74, pp. 843-856.
"Instructions Manual for the Force 2 Electrosurgical Generator", Valleylab/TycoHealthcare Group LP, Boulder, Colorado 1999.
PCT/IL11/00256 International Search Report.
PCT/IL11/00170 International Search Report.
PCT/IL10/00751 International Search Report.
PCT/IL2006/00679 International Search Report.

\* cited by examiner

VIEW C

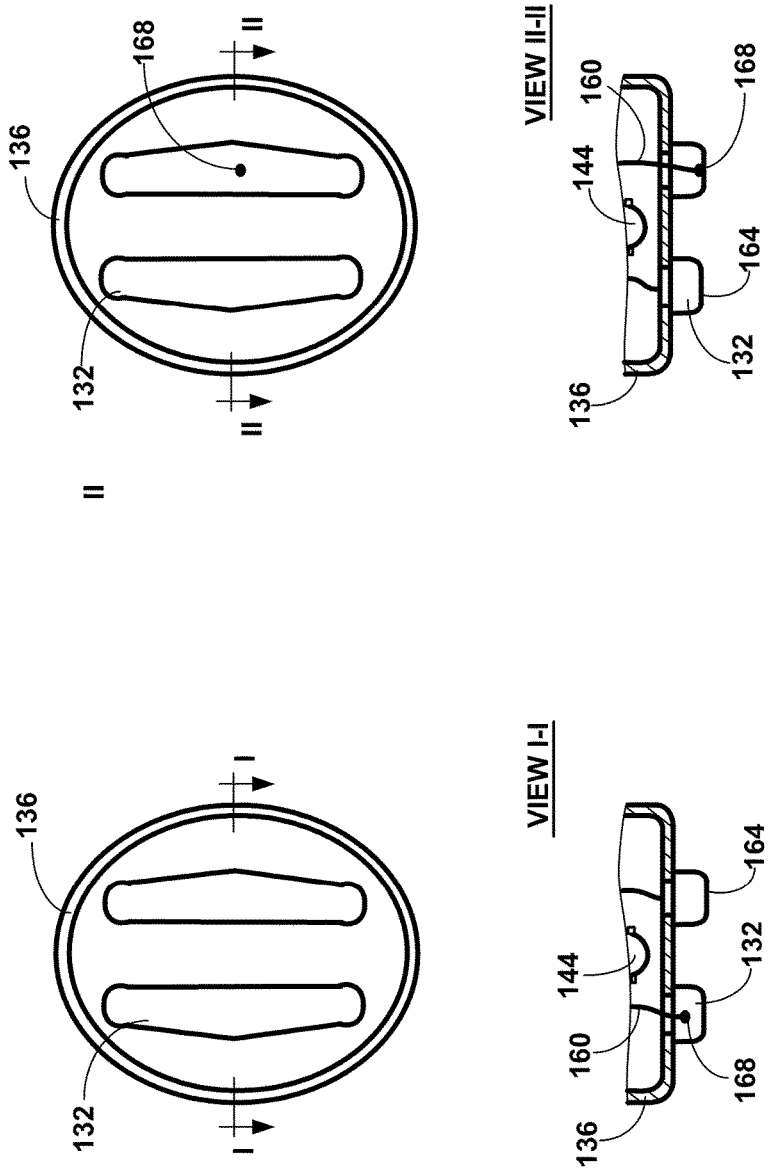

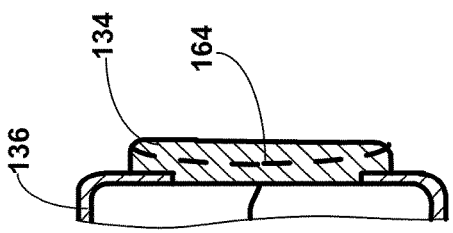
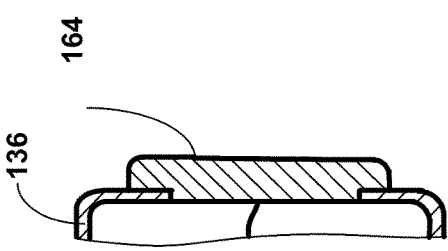
FIG. 5B
FIG. 5A

SKIN TREATMENT APPARATUS FOR PERSONAL USE AND METHOD FOR USING SAME

CROSS-REFERENCE TO RELATED APPLICATIONS

This application is being filed under 35 USC 111 and 37 CFR 1.53(b) as a divisional application to patent application filed in the United States on Feb. 18, 2009 now U.S. Pat. No. 8,606,366 and assigned Ser. No. 12/388,309.

TECHNOLOGY FIELD

The method and apparatus are related to the field of personal cosmetic procedures and in particular to wrinkle removal procedures.

BACKGROUND

External appearance is important to most people. In recent years, methods and apparatuses have been developed for different cosmetic treatments. Among these are hair removal, treatment of vascular lesions and skin rejuvenation. In these treatments, a volume of skin tissue under the skin is heated to a temperature that is sufficiently high as to achieve a desired skin effect. The temperature producing the desired effect is typically in the range of 38-60 degrees Celsius. One method that has been used for heating the epidermal and dermal layers of the skin is pulsed or continuous radio-frequency (RF) energy. In this method, electrodes are applied to the skin and an RF voltage pulse is applied across the electrodes. The properties of the voltage pulse are selected so as to generate an RF current pulse which heats the tissue to the required temperature.

Presently, a number of light based skin surface or deeper skin layer treatments have been developed. These treatments typically use laser diodes, LED, Xenon lamp (Intense Pulsed Light or IPL) or incandescent lamp radiation to irradiate a surface of skin where vascular lesions, varicose veins, acne, mole marks and similar disorders are present. The optical radiation may have a single wavelength or several wavelengths. The wavelengths are selected to be optimal for the color of the contrasted component of the target skin segment, and are typically in the range of 400 to 1800 nm.

The above described equipment is both costly and bulky. It is typically operated in an ambulatory set-up by a qualified operator and frequently requires the presence of medical personnel specialized in such treatments. There is a need on the market for a small size, low cost, and safe to use apparatus that may be operated by the user and enable the user to use the equipment and get results similar or identical to those achieved by professional equipment skin treatments.

BRIEF SUMMARY

An apparatus for personal cosmetic skin treatment including an RF generator and an applicator with at least a pair of electrodes mounted on the distal end of the applicator. The electrodes are configured for applying an RF voltage to a subject skin. The RF generator is configured to supply a number of RF voltage types to the electrodes. A source of light is arranged between electrodes and illuminates the skin segment between the electrodes. The applicator is moved over the skin in a scanning movement applying RF voltage to the segment of skin between the electrodes. The source of light operates concurrently or sequentially with the RF generator and illuminates the same segment of skin.

BRIEF LIST OF DRAWINGS

The apparatus and the method are particularly pointed out and distinctly claimed in the concluding portion of the specification. The apparatus and the method, however, both as to organization and method of operation, may best be understood by reference to the following detailed description when read with the accompanying drawings, in which like reference characters refer to the same parts throughout the different views. The drawings are not necessarily to scale, emphasis instead being placed upon illustrating the principles of the method.

FIGS. 1A and 1B, jointly referred to as FIG. 1, are schematic illustrations of an exemplary embodiment of the apparatus for personal skin treatment.

FIGS. 4A and 4b, jointly referred to as FIG. 4, are schematic illustrations of some exemplary electrode-thermocouple configurations of the applicator.

Figure 5C:
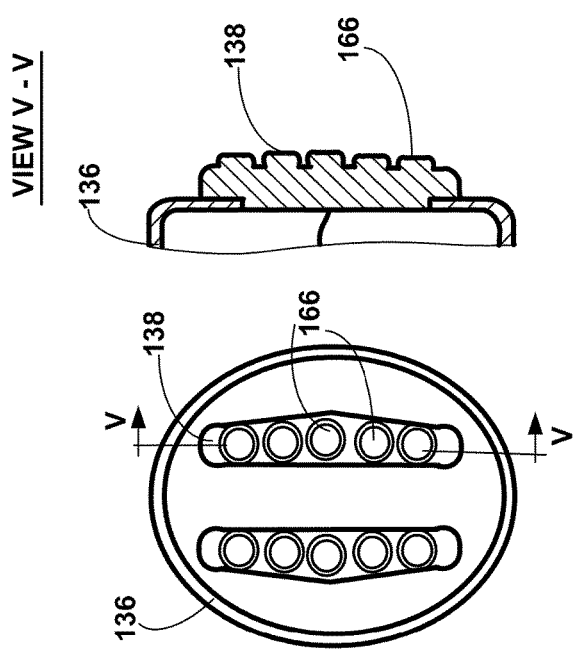

FIGS. 5A, 5B and 5C, jointly referred to as FIG. 5, are schematic illustrations of some additional exemplary applicator electrode configurations.

Figure 6:
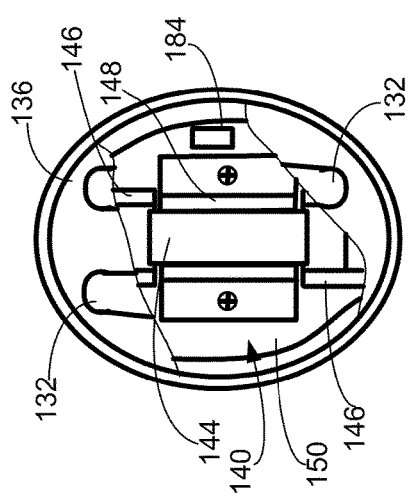

FIG. 6 is a schematic illustration of a cross section of the applicator of FIG. 1 in plane perpendicular to longitudinal axis of the applicator.

Figure 7:
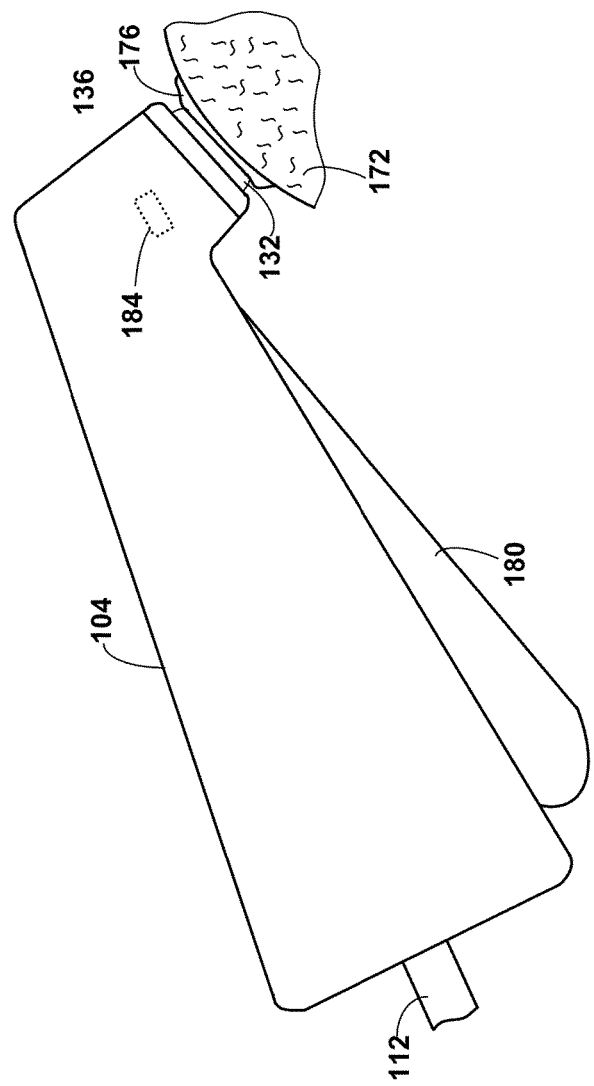

FIG. 7 is a schematic illustration of an applicator with a built-in gel dispenser.

Figure 8:
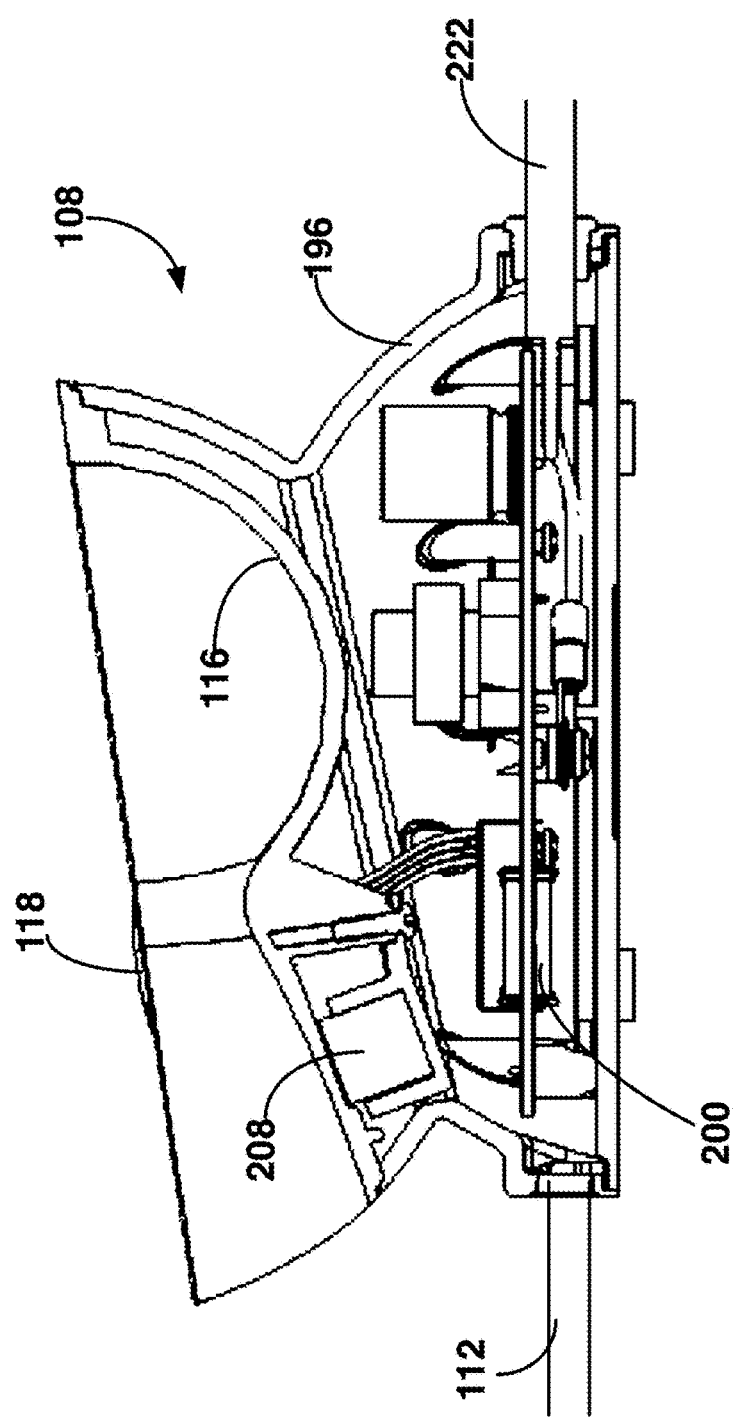

FIG. 8 is a schematic illustration of a cross section of the docking stand of the apparatus for skin treatment.

Figure 9:
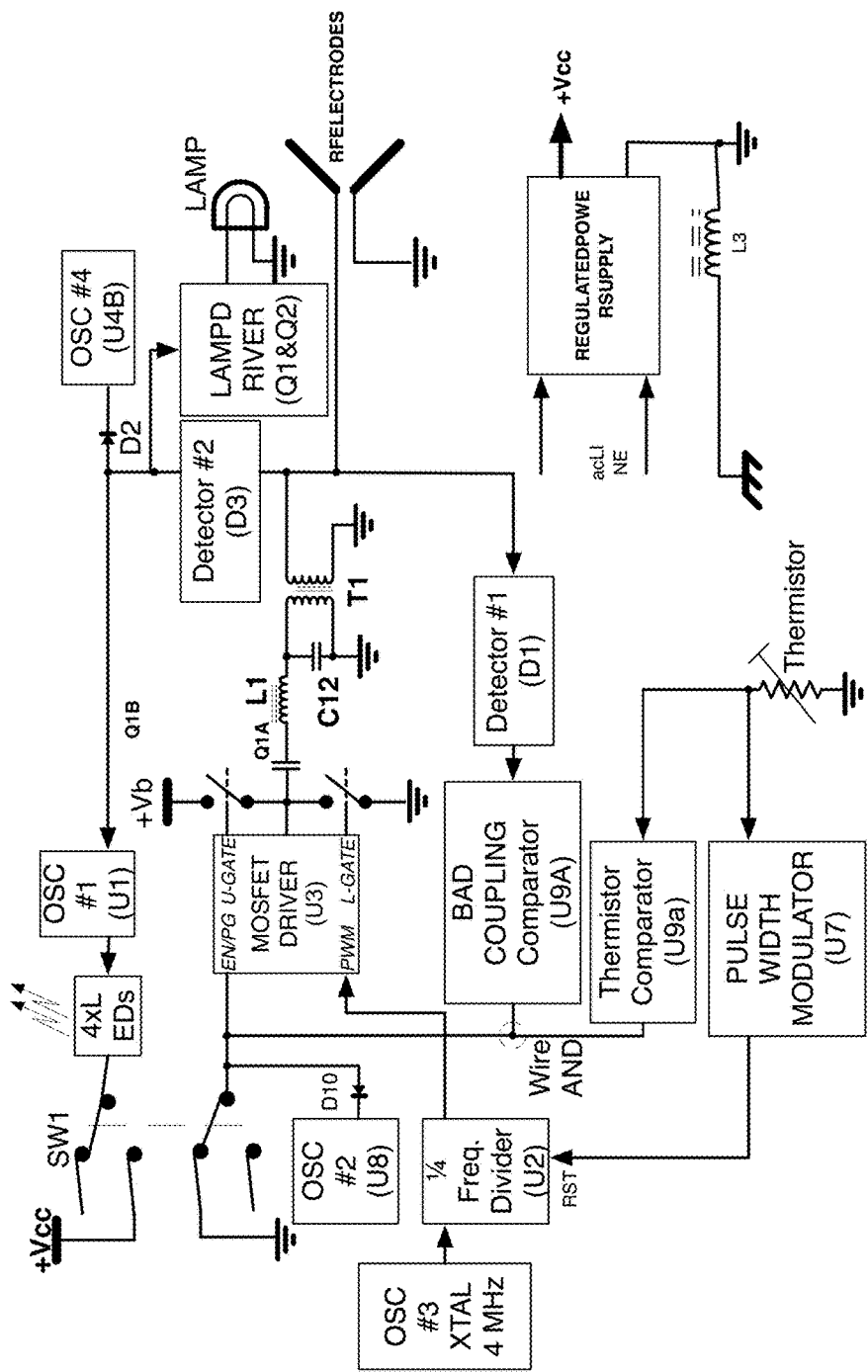

FIG. 9 is a schematic illustration of an exemplary embodiment of the electronic circuit of the apparatus for skin treatment.

Figure 10:
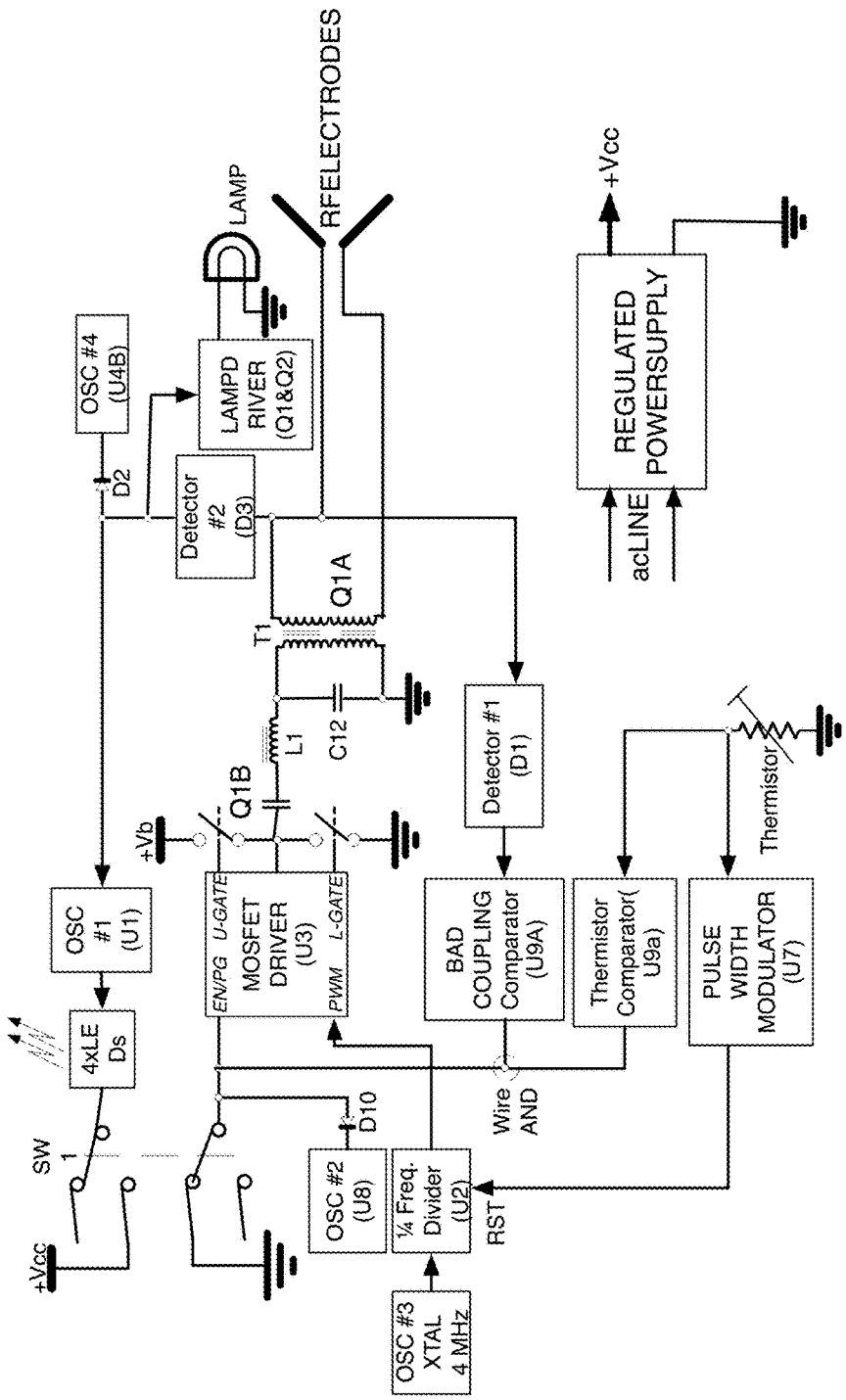

FIG. 10 is a schematic illustration of another exemplary embodiment of the electronic circuit of the apparatus for skin treatment.

Figure 11:
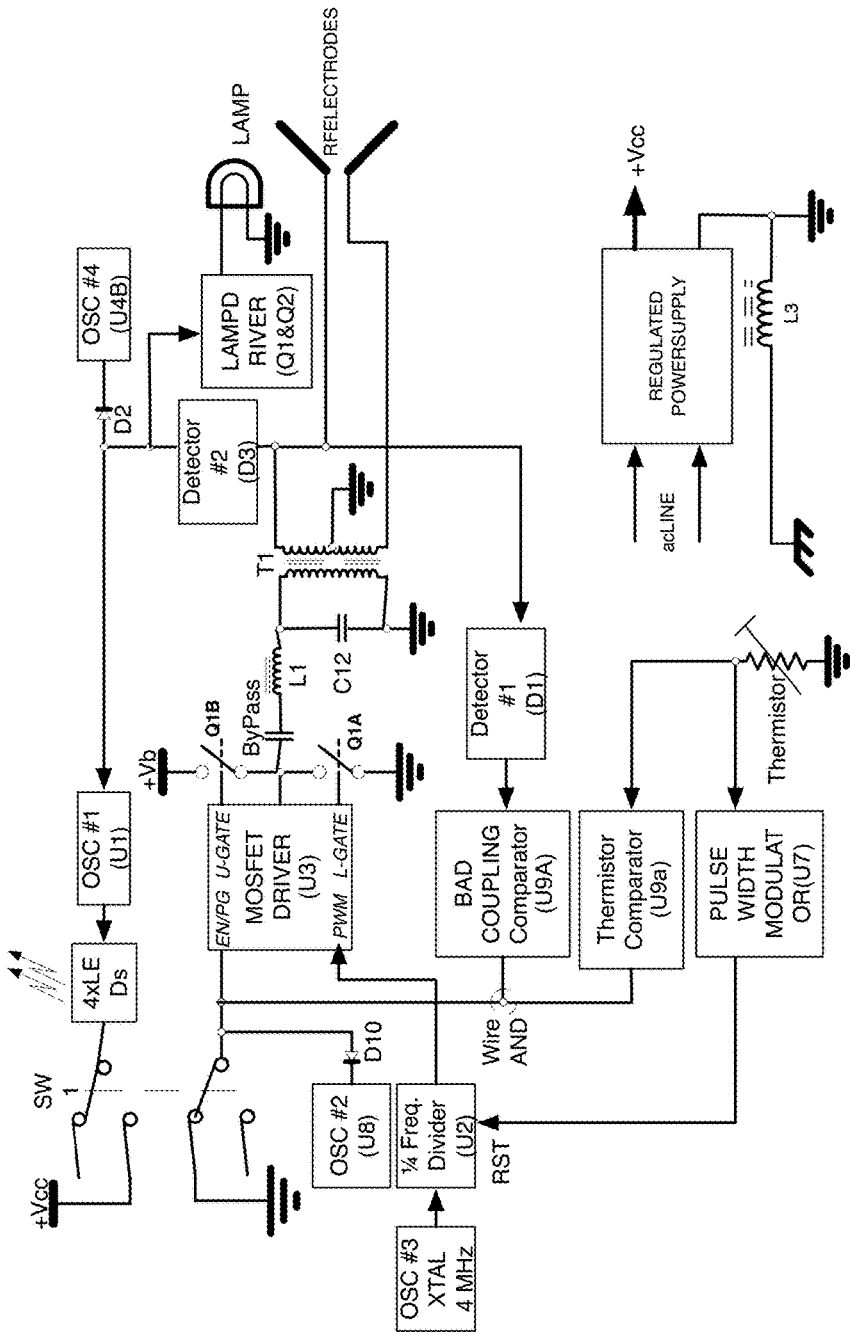

FIG. 11 is a schematic illustration of an additional exemplary embodiment of the electronic circuit of the apparatus for skin treatment.

Figure 12:
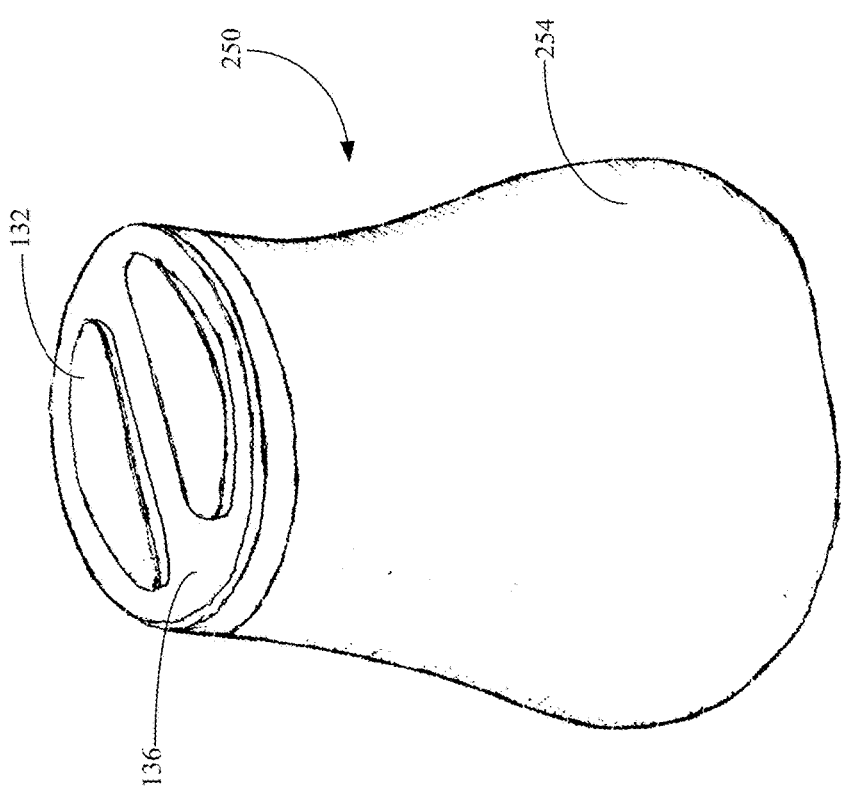

FIG. 12 is a schematic illustration of an additional embodiment of the apparatus for personal skin treatment.

Figure 13:
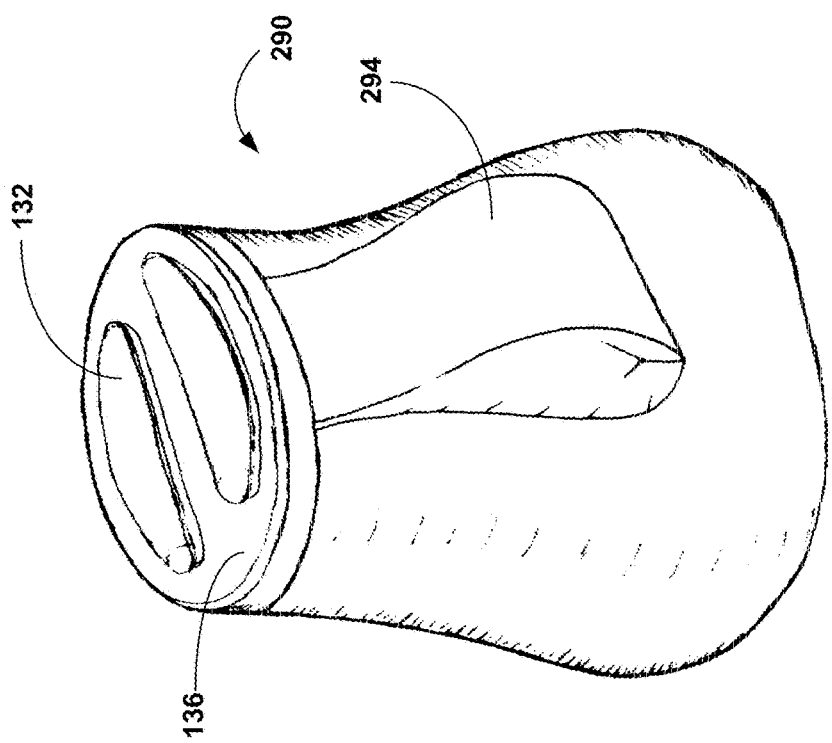

FIG. 13 is a schematic illustration of a further embodiment of an apparatus for personal skin treatment with a built-in gel dispensing arrangement.

Figure 14:
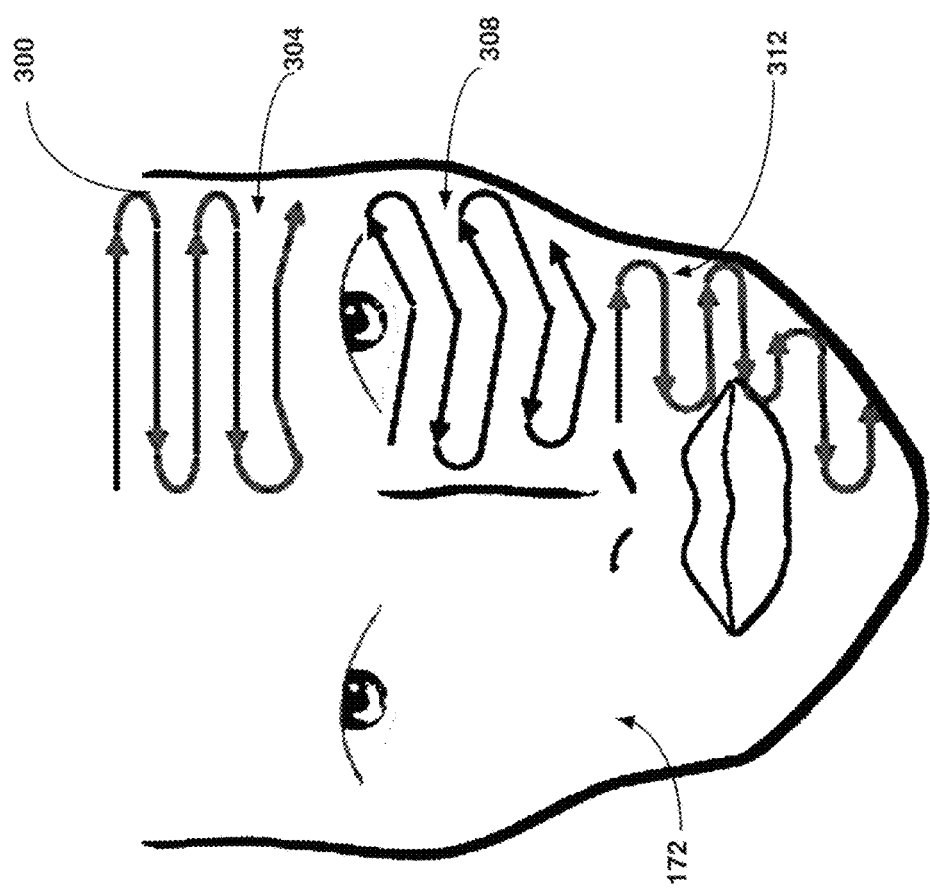

FIG. 14 is a schematic illustration of typical skin treatment scanning movements of the applicator.

DETAILED DESCRIPTION OF THE EXEMPLARY EMBODIMENTS

In the following detailed description, reference is made to the accompanying drawings which form a part hereof. This is shown by way of illustrating different embodiments in which the apparatus and method may be practiced. Because components of embodiments of the present apparatus can be positioned in a number of different orientations, the directional terminology is used for purposes of illustration and is in no way limiting. It is to be understood that other embodiments may be utilized and structural or logical changes may be made without departing from the scope of the present method and apparatus. The following detailed description, therefore, is not to be taken in a limiting sense, and the scope of the present apparatus and method is defined by the appended claims.

As used herein, the term "skin treatment" includes cosmetic skin treatment of various skin layers such as stratum corneum, dermis, epidermis, skin rejuvenation procedures, wrinkle removal, and such procedures as collagen shrinking or destruction. The term "skin surface" relates to the most external skin layer, which may be stratum corneum.

Figure 1A:
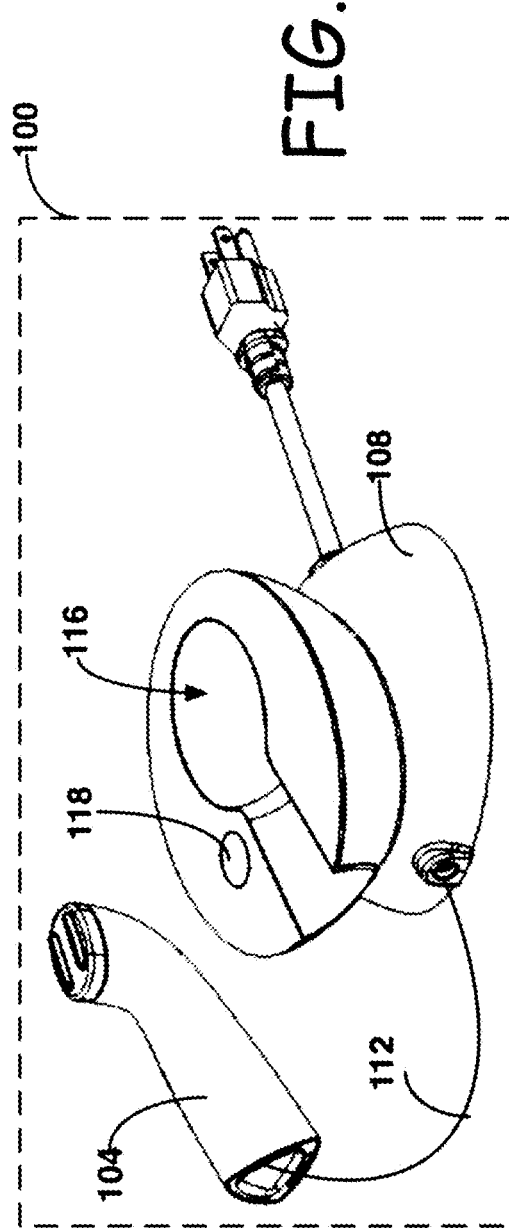
Figure 1B:
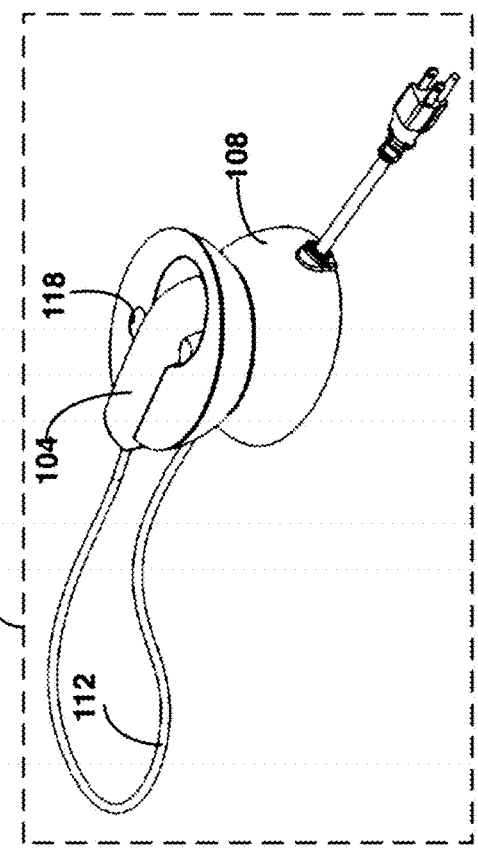

Reference is made to FIG. 1, which is a schematic illustration of an exemplary embodiment of the apparatus for personal skin treatment. Apparatus 100 (FIG. 1A) comprises an applicator 104 adapted for sliding movement on a subject skin, a docking stand 108 on which the applicator is placed when not in use (FIG. 1B) and harness 112 connecting applicator 104 and stand 108. Harness 112 enables electric or other type of communication between applicator 104 and stand 108. When not in operation, applicator 104 may be located in a docking bay 116 (FIG. 1B) of stand 108. Apparatus 100 may receive power supply from a regular electric supply network receptacle, or from a rechargeable or regular battery. Lamp 118 indicates operational status of stand 108.

Figure 2:
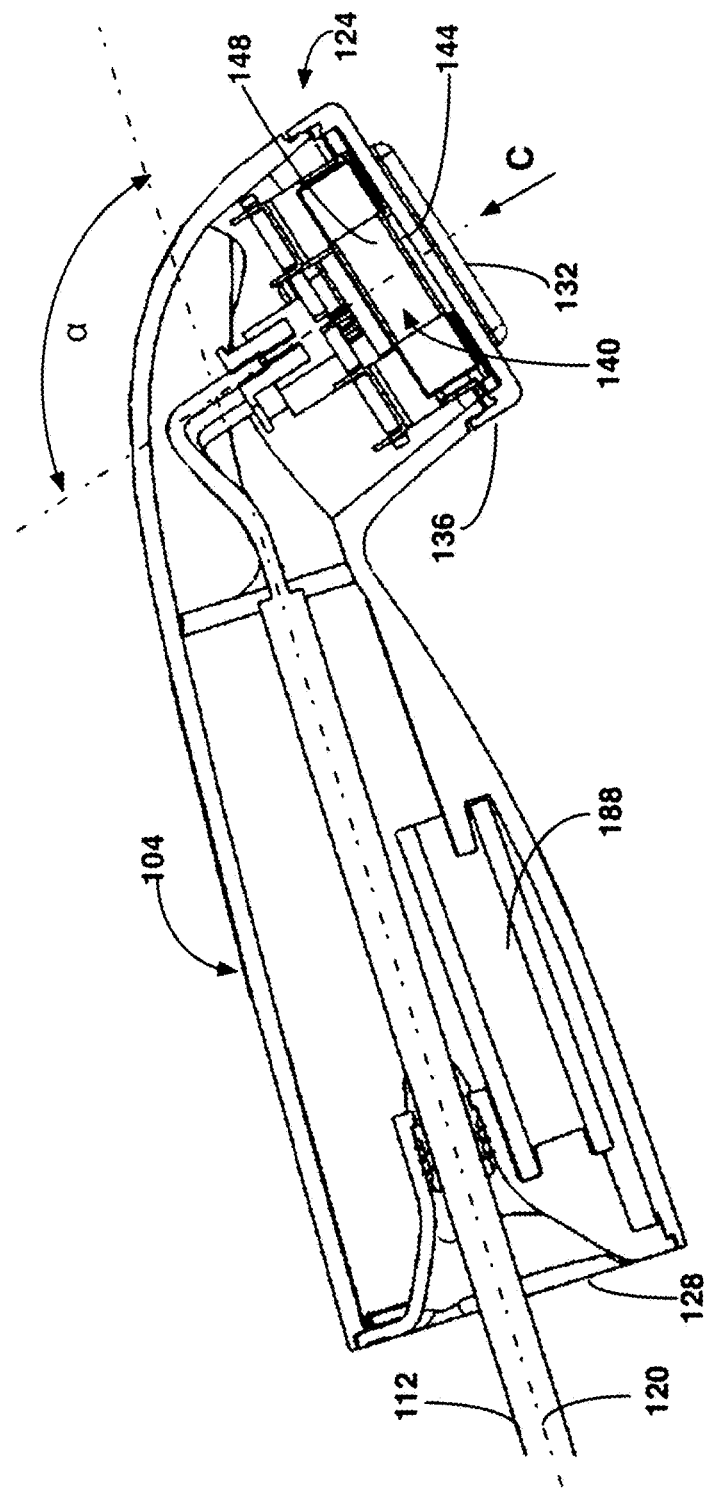
FIG. 2 is a schematic illustration of a cross section along the longitudinal axis of an exemplary embodiment of the applicator of the apparatus of FIG. 1.

FIG. 2 is a schematic illustration of a cross section along the longitudinal axis of the applicator of the present apparatus. Applicator 104 is shown to have body or handle, ergonomically shaped or suitably shaped for holding with the hand, and having a longitudinal axis 120 with extending and projecting forward distal end 124 and a proximal end 128. Distal end 124 is typically oriented at an angle α degrees to axis 120. Angle α is selected to enable proper contacts between electrodes 132 and a target area of skin or material to be treated, and at an angle to facilitate convenience in holding applicator 104. For instance, the angle α may be about 110 degrees. Mounted on distal end 124 of the applicator 104 are one or more RF applying electrodes 132 connected through harness 112 to a source of RF voltage (not shown) located in stand 108. An optical filter 136 serves as a mounting basis for electrode 132. Optical filter 136 also serves as an operation indicator of applicator 104. Optical filter 136 is typically a broadband glass or plastic filter that transmits red and infrared wavelength and typically lights with a reddish or first color.

Mounted at the distal end 124 of applicator 104 is a source of light 140 that may be an incandescent lamp 144 or an incandescent lamp optimized (doped) for emission of red and infrared radiation. The useful spectrum of lamp 144 may be in the range of 400 to 1800 nm and emitted optical energy in the range of 1W to 20W. A reflector 148 collects and directs radiation emitted by lamp 144 towards a segment of skin to be treated. Alternatively, an LED emitting one or more suitable wavelengths or a semiconductor laser may be used instead of lamp 144. When LEDs are used as radiation emitting sources their wavelengths may be selected such that one of them will serve as an operation indicator of first color canceling the need for a special filter. The remaining LEDs may provide the wavelengths required for the treatment. A single LED with multiple emitters may also be used. Shown is a magnetic or a ferromagnetic insert 188 cooperating with magnet 208 (FIG. 8) and holding applicator 104 in docking bay 116 (FIGS. 1 and 8) of stand 108.

Figure 3:
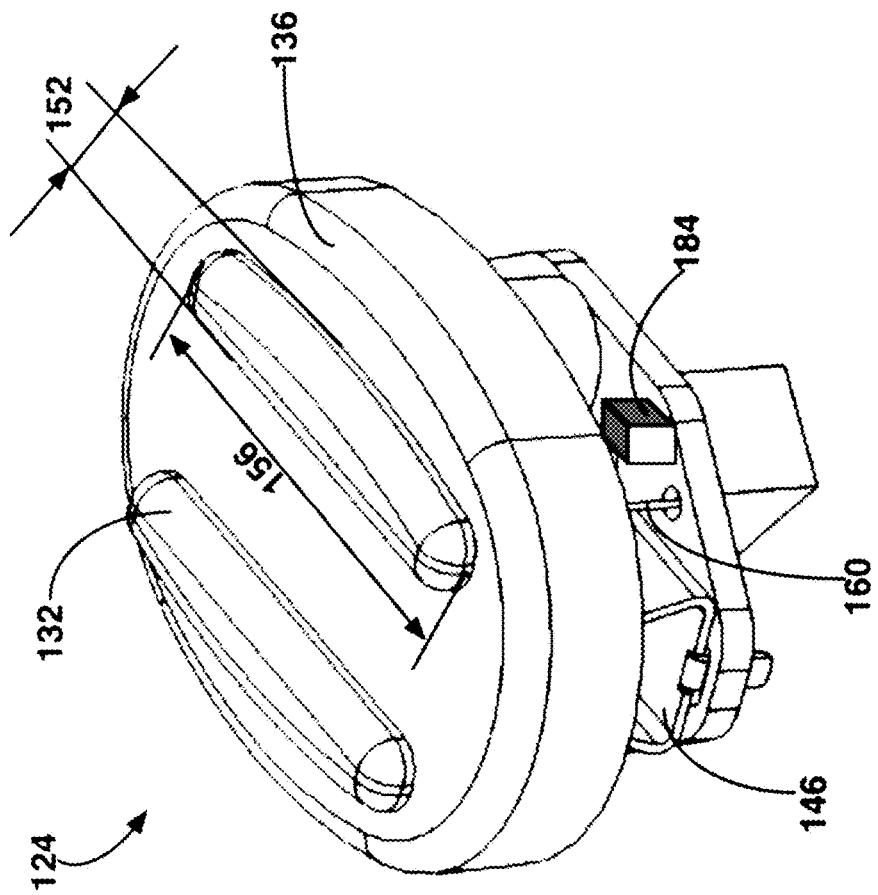
FIG. 3 is a schematic three-dimensional illustration of an exemplary embodiment of a distal end of the applicator.

FIG. 3 is a schematic three-dimensional illustration of an exemplary embodiment of the distal end 124 of applicator 104. FIG. 3 illustrates electrodes 132 mounted on filter 136, thermocouple 160 built-in into at least one of the electrodes 132, and lamp holder 146. Electrodes 132 typically have an elongated body with width 152 to length 156 ratio of at least 1:5. The geometry of the electrodes is optimized to selectively heat the skin in the area between the electrodes. Electrodes 132 typically have rounded edges in order to avoid hot spots on the skin surface near the edges of the electrodes. Rounded electrodes also allow smooth movement of applicator 104 (FIG. 1) over the skin surface. FIG. 3 illustrates a bi-polar electrode system, although a uni-polar electrode system (not shown) may be used. Alternatively, when more than one electrode 132 is used the bi-polar or uni-polar system may be generated by feeding a proper RF voltage to the electrodes.

FIG. 4 is a schematic illustration of some electrode-thermocouple configurations of the applicator. In the embodiment illustrated in FIG. 4A, one or more electrodes 132 may have a built-in thermocouple 160 residing with the temperature-sensing end 168 inside electrode body 132. In another embodiment, shown in FIG. 4B, the temperature-sensing end 168 of thermocouple 160 may be flush with electrode 132 contacting skin surface 164. In some embodiments a thermistor may be used instead of the thermocouple. The thermistor may be embedded into one or more electrodes, or as a standalone probe being in contact with the treated skin segment. Thermocouple 160 having a temperature sensing end flush with electrode 132 surface 164 measures skin temperature, where residing within electrode 132 end of thermocouple 160 measures only electrode 132 temperature. Thermocouple 160 communicates the measured temperature to a feedback loop of RF voltage generator 200 (FIG. 8). Based on temperature values, RF voltage generator 200 may increase or decrease RF voltage amplitude, change the duty cycle of the RF voltage supplied to electrodes 132, or even switch off the RF voltage generator.

FIG. 5 is a schematic illustration of some electrode configurations of applicator 104. In one embodiment (FIG. 5A), electrode 132 is a solid electric current conducting body. In another embodiment (FIG. 5B), electrode 134 may be a flexible electric current conducting body. A flexible electrode is capable of adapting its shape to the contours of the treated subject skin enabling a better contact with the skin. In an additional embodiment (FIG. 5C), electrode 138 may have a relief 166 on the skin contacting surface 164. The relief may be a plurality of microelectrodes or a plurality of macro electrodes.

FIG. 6 is a schematic illustration of a cross section of the applicator of FIG. 1 in plane perpendicular to longitudinal axis of the applicator. It further demonstrates the construction of light source 140. Lamp 144 and reflector 148 are located between electrodes 132. Filter 136 protects lamp 144 and cuts out of the lamp emission a desired spectral range out of a spectrum emitted by lamp 144. The listed elements are assembled on a type of printed circuit board support 150. The illustrated embodiment also shows the inclusion of an optional accelerometer 184.

In order to improve the coupling of RF induced current to the skin 172 (see FIG. 7) it is desirable to cover skin 172 by a layer of gel 176 improving electric contact between electrodes 132 and skin 172 and facilitating electrode on skin gliding. Typically, gel 176 is dispensed over skin 172 before the treatment, and remains on the skin during the treatment. Gel dispensing, in addition to skin cleaning performed by water and soap or other cleaning means, represents a skin pretreatment operation. According to one embodiment, gel 176 may be dispensed manually. A disposable flexible container actuated manually by the user squeezes and dispenses gel 176 over skin 172. In a further embodiment, gel dispenser 180 may be a part of applicator 104 and is actuated automatically during treatment from a disposable or refillable container. Alternatively, gel dispenser may be located in stand 108. Where gel dispenser is located in stand 108, harness 112 (FIG. 1) in addition to electrical lines may contain a suitable tubing for supplying gel 176 to distal end 124 of applicator 104 and skin 172. In order to enable good contact and facilitate the treatment gel 172 may have an electrical resistance higher than the skin being treated.

Applicator 104 may include an accelerometer 184, similar to the accelerometer of FIG. 6, which could detect and provide an indication of the movement of applicator 104 and the speed of the movement. Accelerometer 184 communicates with RF voltage generator 200 (see FIG. 8). Based on the changes in the speed of advance (acceleration) of applicator 104, RF voltage generator 200 may increase or decrease RF voltage amplitude or change the duty cycle of the RF voltage supplied to electrodes 132, enabling optimal maintenance of the treatment temperature.

FIG. 8 is a schematic illustration of a cross section of the docking stand of the apparatus for providing skin treatment. Stand 108 may be an aesthetic looking plastic or metal enclosure 196 incorporating an RF voltage generator 200, an operation indicator 118, and a permanent or electric magnet 208 for holding or securing the applicator 104 with in the docking stand at a particular position. In some embodiments, the RF voltage generator may be located in the applicator 104. Operation indicator 118 may be a lamp similar to lamp 118 having a second color different from the first color of lamp 144. Operation indicator 118 may also serve as a stand-by mode indicator. The lamp or a LED providing the second color may be greenish or bluish. A glass or plastic filter may be used so that a simple incandescent lamp can be used as an indicator. Stand 108 may receive power supply from a regular electric network receptacle with the help of power cord 222 or be equipped by rechargeable batteries.

RF voltage generator 200 has at least one feedback loop operated by a signal received from thermocouple 160 (see FIG. 4). The same or an additional feedback loop may be operated, as explained above, by a signal provided by accelerometer 184 (see FIG. 3 and FIG. 6). Alternatively, the impedance of the treated skin segment may be monitored and used for Automatic RF Power Control (APC). It is known that RF generator output depends on the load. It is desirable to maintain the load flat or uniform during operation. This is, however, possible only in a certain range of treated skin impedance and it may be desirable to operate apparatus 100 in a mode that minimizes skin impedance changes. It is also known that skin parameters vary widely between different treated subjects. A typical range of impedance changes may be from 50 to 400 ohm. (It is necessary to mention that electrode configuration may affect impedance range.) Even for the same person, the impedance of the skin located proximate to the forehead and cheek may be substantially different. The type of contact between the electrodes and skin also affects impedance value. An electrode may contact the skin with its entire surface or only partially, depending on skin relief of the face segment. The feedback loops, and in particular the impedance-based loop, allows constant RF power output to be maintained for all the range of skin impedances. Practically, the impedance of the treated skin segment is constantly monitored and the RF power is adjusted accordingly.

FIG. 9 is a schematic illustration of an exemplary embodiment of the electronic circuit of the apparatus 100 for skin treatment. Typically, the treated subject is isolated from the Earth of power supply network. When both RF electrodes are applied to the skin of the subject, the skin, being a conductor, short circuits the electrodes and provides a pass for the RF induced current. Conductive gel that has a resistance higher than the skin facilitates this current pass. In this particular implementation, one of the electrodes is connected to the ground through an inductor L3. The resulting bi-polar RF electrodes create a zero potential at one electrode while the other electrode relative to ground is at maximum potential.

FIG. 10 is a schematic illustration of another exemplary embodiment of the electronic circuit of the apparatus for skin treatment. This particular embodiment discloses a design where RF electrodes are not grounded at all. When the RF electrodes touch the subject skin, an RF current flows through the skin between the electrodes. The bipolar RF electrodes create a minimum potential between them in the middle, regardless of the potential of the subject with respect to ground.

FIG. 11 is a schematic illustration of an additional exemplary embodiment of the electronic circuit of the apparatus for skin treatment. In this case, the output RF generator stage contains a transformer with a secondary center tap connected to ground-earth through an inductor L3. This enables a zero potential to be obtained relative to ground in the middle of the span between the electrodes.

All of the above disclosed electronic schemes enable supply of the required RF power to the electrodes and avoid subject electric shock even if the subject is in contact with the Earth.

FIG. 12 is a schematic illustration of an additional embodiment of the apparatus for personal skin treatment. Apparatus 250 is a convenient-to-hold body 254 incorporating the applicator and stand elements. Apparatus 250 may be plugged into a conventional electric power supply network or be battery operated. The battery may be rechargeable. All earlier described apparatus 100 (FIG. 1) components are mutatis mutandis applicable to apparatus 250. Operation of apparatus 250 is similar to operation of apparatus 100. When the RF electrodes touch the subject skin, apparatus 250 is activated and an RF induced current flows through the skin between the electrodes. When there is no contact between the electrodes and the skin apparatus 250 is in stand-by mode. Optionally, apparatus 250 may have an ON-OFF switch to switch it off completely.

FIG. 13 is a schematic illustration of a further embodiment of an apparatus for personal skin treatment with built-in gel dispensing arrangement. According to one embodiment, apparatus 290 may have a receptacle for a disposable flexible gel container 294. The gel may be dispensed over the skin manually by application of pressure to container 294. In a further embodiment, gel dispenser (not shown) may be a part of apparatus 290 or a type of an automatic dispenser, which pulls gel required for the treatment out of a disposable or refillable container.

The method of skin treatment using the present apparatus will be explained now. Following cleaning and gel spreading over a target segment of skin 172, applicator 104 is placed over the skin segment 172 such that electrodes 132 are in contact with skin 172. Practically, the skin 172 becomes a conductor automatically closing the circuit and enabling an RF current passage between electrodes 132. Induced by RF voltage, current passes through skin 172 and heats it to a desired temperature. RF voltage is applied to electrodes 132 in a continuous or quasi-continuous mode and with duration of at least 0.5 second.

FIG. 14 is a schematic illustration of typical skin treatment scanning movements of the applicator. Applicator 104 may be moved in a type of reciprocal scanning motion as shown by arrows 300 over the skin 172 to treat next skin segment 312. In the course of movement of the applicator it maintains contact between electrodes 132 and skin 172 and delivers a continuous RF power inducing current to treated skin segments 304-312 located between electrodes 132.

Applicator 104 (or apparatus 250) is displaced over the skin segment to be treated so that RF induced current heats the treated skin segment to a temperature that produces the desired treatment of the skin, for example, stimulating the process of collagen remodeling in the skin. Typically, the RF power applied across electrodes 132 can range from 1 W to 20 W but, it is anticipated that other values and ranges may also be applied. The RF power is applied in a continuous or quasi-continuous mode for a period of time, such as at least 0.5 second as a non-limiting example. Applied in this mode, RF power is capable of heating skin from a normal skin temperature to a temperature of about 60 degrees Celsius. It should be noted that the typical treatment time per skin segment is based on several factors. One such factor is the characteristics of the treated skin segment. For example, a bony area with thin skin, like the forehead (segment 304) versus thicker skin in a non-bony segment, such as the area around the eyes (segment 308);. Another factor includes the average surface area per segment. For example, each cheek, jaw line and chin area (segment 312) will require more time than any of the other areas, each of which is effectively smaller than segment 312. In an exemplary treatment process it may be desirable to spend the necessary time on each treatment zone until the desirable treatment end-point is reached. The treatment end-point may be characterized among others by erythema and a significant heat sensation with possible edema and a tightening feeling. The treatment may be continued for an additional 1-2 minutes stabilizing the treatment effect.

During treatment, skin and electrode temperature sensors or acceleration sensors, or impedance monitoring provide an input to the feedback loops of RF voltage generator 200 (see FIG. 8). Based on input of at least one of the sensors feedback, the RF power automatically changes providing and maintaining optimal treatment conditions. The RF voltage changes may include amplitude changes, voltage application time changes or voltage application duty cycle changes. For example, upper and lower treatment temperature limits may be set. If the feedback indicates that the first or upper temperature limit, which may be set for skin temperature exceeding 44 degrees Celsius, automatic reduction in RF power or change of the applied RF power duty cycle may take place. The duty cycle may be reduced to 60% of the maximal operating value. A complete switch-off of the RF power at a second or upper temperature limit, for example at temperature exceeding 45 degrees Celsius may take place. The RF power may also be changed in response to changes in the scanning speed of the applicator 104 as reported or determined by signals received from accelerometer 184. Despite certain RF power reduction, the treatment may continue because, in order to get proper treatment results, it is desired not only to reach a certain temperature in the tissue, but to maintain it for some threshold period of time. To satisfy this requirement, the decrease in RF power may not exceed 30% or 40% of the maximal allowable RF power. At the reduced RF power level, the existing natural blood flow may dissipate sufficiently to affect the temperature in the skin. The second or upper temperature limit is primarily a safety limit preventing damage to the skin.

A person treating his own skin with apparatus 100 may simply displace applicator 104 (or apparatus 250) over the skin surface in the segment of skin to be treated at a reasonable speed where the temperature or acceleration feedback will adjust the RF power to obtain the desired treatment result. Known methods of monitoring the skin impedance between electrodes 132 and allowing the temperature of the skin between the electrodes to be followed by changing RF power may be also applied to the present treatment method. It is known that temperatures of about 40 degrees Celsius and lower do not cause the desired skin treatment effect. In cases where the user moves applicator 104 faster than desired, the temperature and acceleration feedback systems adjust the RF power to get a desired treatment effect. An audible signal alerting the user on the desired temperature or acceleration may be generated by a buzzer located in stand 108.

Temperature and acceleration feedback loops automatically adjust the treatment parameters to the electrical properties of the treated person's skin. These feedback loops avoid an undesired rise in temperature of the skin and limit the skin heating. The loops provide signals to the user to indicate the presence of conditions under which the treatment is not effective. Such notice enables the user to correct the treatment parameters. All of these features, or the inclusion of a subset of the described features, when incorporated into an embodiment make apparatus 100 ideal for personal use in residential apartment conditions or the like.

Generally, the user may use and operate apparatus 100 or apparatus 250 according to the present method for skin rejuvenation, collagen remodeling and contraction, skin tightening, wrinkle treatment, subcutaneous tissue treatment, cellulite treatment, pore size reduction, skin texture and tone improvement, acne treatment and hair removal.

The method of skin treatment presented may be further enhanced by applying red and infrared radiation generated by lamp 144 (FIGS. 2 and 6) to the surface of the treated segment of the skin 172. This allows treatment of such skin targets as vascular lesions, varicose veins, acne, and mole marks. The optical energy of the lamp or similar optical energy source may have a value of 1W to 10W and be applied for a time similar to that of RF application. Actually, simultaneous treatment of skin and skin surface may have mutually beneficial effects. It reduces the risk of adverse effects associated with light only based treatment, and use of RF energy is advantageous in treating most skin types since this form of energy is not sensitive to skin pigmentation.

The skin post-treatment process includes at least gel removal from the skin, cleaning the skin surface treated and if necessary application of a moisturizing cream to reduce post treatment effects.

A number of embodiments have been described. Nevertheless, it will be understood that various modifications may be made without departing from the spirit and scope of the method. Accordingly, other embodiments are within the scope of the following claims:

What is claimed is:

1. A method of skin treatment, said method comprising:
   a) applying an applicator with at least a pair of electrodes mounted on a distal end of the applicator, to a segment of subject skin to be treated;
   b) supplying said electrodes with an RF voltage generated by an RF voltage generator with an output stage that includes a transformer with a secondary center tap connected to ground earth through an inductor to obtain a zero potential in the middle of the span of the electrodes with respect to the ground; and
   c) enabling a contact between said electrodes and said skin and short circuiting said electrodes enabling a RF current to pass through the skin between said electrodes, and moving said applicator in a scanning movement over a segment of the skin to be treated.

2. The method of skin treatment according to claim 1, further comprising a source of light located between the electrodes and configured to apply red and infrared radiation to the same segment of the skin.

3. The method of skin treatment according to claim 1, wherein said RF power is from 1 W to 20 W and has a frequency from 300 kHz to 50 MHz.

4. The method of skin treatment according to claim 1, wherein said RF power is applied in a continuous or quasi-continuous mode for at least 0.5 sec.

5. The method of skin treatment according to claim 1, wherein sensors are sensing at least one of a group of electrode temperature, skin temperature, and skin impedance and wherein the RF power automatically changes, based on input of at least one of said sensors.

6. The method of skin treatment according to claim 5, wherein said automatic changes in the RF power are at least one of the changes of RF duty cycle, RF voltage, switch-off of the RF, and change of scanning speed.

7. The method of skin treatment according to claim 5, wherein said automatic changes in the RF power take place at first skin temperature or at second skin temperature and wherein the first temperature exceeds 44 degrees Celsius and the second temperature exceeds 45 degrees Celsius.

8. The method of skin treatment according to claim 1 including a skin pretreatment method wherein the skin pretreatment method includes at least spreading of gel over the skin segment to be treated and wherein said gel as electrical resistance higher than said treated skin surface.

9. A method of skin treatment, said method comprising:
a) applying an applicator with an elongated body a portion of which has been adapted for mounting of at least a pair of electrodes adapted to apply RF energy, generated by an RF voltage generator with an output stage that includes a transformer with a secondary center tap connected to ground earth through an inductor, to a segment of subject skin, such that said skin connects the electrodes enabling an RF current to pass between said electrodes;
b) enabling contact between said electrodes and skin and moving said applicator over a segment of the skin to be treated in a scanning movement; and
c) applying concurrently with the RF to the same segment of skin red and infrared radiation.

10. The method of skin treatment according to claim 9, further comprising sensing by one or more sensors at least one of a group of electrode temperature, skin temperature, and skin impedance accompanying said treatment and wherein based on input of at least one of said sensors the RF power automatically changes.

11. The method according to claim 10, wherein automatic changes in RF power take place at first temperature when said temperature exceeds 44 degrees Celsius and the second temperature when said temperature exceeds 45 degrees Celsius.

12. The method of skin treatment according to claim 10, further comprising a skin pretreatment process and a skin post-treatment processes.

13. The skin pretreatment method according to claim 12, wherein said method includes at least gel spreading over the skin surface to be treated has electrical resistance higher than said treated skin surface.

* * * * *